United States Patent [19]

Young et al.

[11] 4,203,947

[45] May 20, 1980

[54] LOAD CONDITIONING CONTROL APPARATUS FOR STEAM STERILIZATION

[75] Inventors: Jack H. Young, Cambridge Springs; Frank E. Halleck, Erie, both of Pa.

[73] Assignee: American Sterilizer Company, Erie, Pa.

[21] Appl. No.: 8,925

[22] Filed: Feb. 2, 1979

Related U.S. Application Data

[62] Division of Ser. No. 850,845, Nov. 11, 1977, Pat. No. 4,164,538.

[51] Int. Cl.² .................. A61L 5/00; A61L 1/00; A61L 3/00
[52] U.S. Cl. .................. 422/114; 422/26; 422/116; 422/295
[58] Field of Search .................. 422/26, 110, 111, 114, 422/116, 295, 34, 27

[56] References Cited

U.S. PATENT DOCUMENTS

| | | | |
|---|---|---|---|
| 2,080,179 | 5/1937 | Merriam et al. | 422/27 |
| 2,131,134 | 9/1938 | Baer et al. | 422/31 |
| 2,188,371 | 1/1940 | Merriam | 131/133 |
| 3,035,886 | 5/1962 | Hickey | 422/27 |
| 3,086,263 | 4/1963 | Huber | 422/116 |
| 3,099,522 | 7/1963 | Lauterbach | 422/116 |
| 3,206,275 | 9/1965 | Sair et al. | 422/33 |
| 3,409,389 | 11/1968 | Bjork | 422/26 |
| 3,436,170 | 4/1969 | Lodge | 422/26 |
| 3,494,725 | 2/1970 | Prons et al. | 422/26 |
| 3,598,516 | 8/1971 | Shull et al. | 422/27 |
| 3,795,483 | 3/1974 | Graffingholt | 422/26 X |
| 3,954,406 | 5/1976 | Chamberlain | 422/27 |
| 3,982,893 | 9/1976 | Joslyn | 422/111 X |
| 4,003,703 | 1/1977 | Montgomery et al. | 422/26 X |

FOREIGN PATENT DOCUMENTS 542554  1/1942  United Kingdom.

OTHER PUBLICATIONS

S. S. Block, "Disinfection Sterilization and Preservation," Publ. by Lee & Febiger, Phila., Pa., 1977, pp. 493-508.
J. J. Perkins, "Principles & Methods of Sterilization in Health Sciences," Publ. by C. C. Thomas, Springville, Ill., pp. 110-114, 150-152 & 501-530.
"Developments in Industrial Microbiology," vol. 18, Soc. for Industrial Microbiology, pp. 335-351.

*Primary Examiner*—Barry S. Richman
*Attorney, Agent, or Firm*—Raymond N. Baker

[57] ABSTRACT

Methods and apparatus for steam sterilization in which goods are conditioned by removing air and heating to a desired temperature in sealable chamber. Pressure change in the chamber is monitored and employed to control conditioning. The goods are subjected to a plurality of controlled cyclic pressure pulses below a predetermined supra-atmospheric pressure level by alternate evacuation and vapor pressurization of the chamber. The cyclic pressure pulsing is made responsive to load characteristics which are determined by monitoring pressure change rate in the chamber. In a specific embodiment, air is flushed from the chamber initially by the injection of steam simultaneously with evacuation; the evacuation phase of each pulse continues until both a predetermined time has lapsed and a predetermined vacuum level has been attained; and, the steam pressurization phase of each pulse is continued until a fixed pressure related to sterilization temperature is reached.

6 Claims, 5 Drawing Figures

LOAD CONDITIONING CONTROL APPARATUS FOR STEAM STERILIZATION

This is a division of application Ser. No. 850,845, filed Nov. 11, 1977 and now U.S. Pat. No. 4,164,538 issued Aug. 14, 1979, the entire disclosure of which is incorporated herein by reference.

This invention is concerned with steam sterilizing operations, including dependable, proficient and accurately monitored removal of air and heating of goods to be sterilized. In particular, the invention is concerned with automated sterilizer control providing for load conditioning at optimum efficiency of time and energy.

Steam sterilization requires steam contact with every portion of the load to be sterilized (Principles and Methods of Sterilization in Health Sciences, John J. Perkins, 2nd Edition, Third Printing, published by Charles C. Thomas, Springfield, Ill., pages 110–114). Therefore proper conditioning of loads which include fabrics requires substantially complete removal of air from the interstices of the fabric in order to eliminate any air pockets and thus provide for heating the load throughout its volume.

Conditioning non-hermetically-sealed loads in prior steam sterilization practice has generally relied on high pre-vacuum treatment or steam pulsing. The high pre-vacuum treatment method relies on drawing a deep vacuum, to as low as a few millimeters of mercury in the load and the sterilizing chamber, in an attempt to substantially completely remove air from the load before the introduction of steam. This approach is costly, both in equipment and operation, since high-powered vacuum pumping apparatus is required and the entire system must have high vacuum integrity. Also, substantial time can be required to reach the high vacuum levels employed, especially with fabric-type loads.

Various steam pulsing methods have been taught (Principles and Methods of Sterilizaton in Health Sciences, supra, pages 150–152; U.S. Pat. No. 3,409,389; and U.S. Pat. No. 3,494,725), including steam pulsing above atmospheric pressure, steam pulsing below atmospheric pressure, and a combination of pulsing above and below atmospheric pressure. As set forth in Principles and Methods of Sterilization in Health Sciences, supra, at page 151:

"The time required to heat the load to sterilizing temperature with a pulsing system depends upon the number of pulses and the time expended for each pulse. The effectiveness of a pulse, and therefore the number of pulses required, is in turn dependent upon the amplitude or excursion of the pulse and the ratio of the maximal and minimal absolute pressures of each pulse. The time expended by a pulse is a function of the rate of delivery and expulsion of steam and of the maximal and minimal pulsing pressures related to atmospheric pressure."

In the past, the conditioning portion of a steam cycle has been based on requirements to heat the most difficult load to be encountered in a particular sterilizer. In practice that sterilizer was then pre-set to carry out the conditioning cycle for the most difficult to heat load regardless of the characteristics or size of the load to be sterilized. In the steam pulsing method, a timer control or a pressure control functioned in a fixed manner, based on a fixed time or a fixed pressure excursion of the pulses. Such an approach can be inefficient when using fixed time cycles to sterilize partial loads or loads containing minimal fabric and when using fixed pressure cycles to sterilize full loads. Alternatives to a cycle based on the most difficult to heat load include operator prejudgement of loads and operator selection of the conditioning cycle, or use of conditioning sensors (e.g., temperature sensors) manually positioned within the load to monitor load conditioning. Such alternatives require operator steps and/or judgements and, therefore, are subject to oversight or error which good hospital practice attempts to avoid.

The present invention teaches a unique concept for automated and accurate conditioning control which provides for monitoring the load without placement of load sensors in contact with the load and without requiring prejudgement of the load by the operator. The invention evaluates load characteristics through rate of pressure change during cyclic pulsing to provide dependable and complete conditioning while enabling conservation of both time and energy. The concepts and procedures of the present invention are applicable to any of the standard sizes of sterilizers used commercially and provide for complete conditioning to facilitate desired sterilization in the shortest practical time and at minimum vacuum levels.

Partial or minimal fabric loads can present the greatest difficulty in obtaining proper air removal and complete conditioning automatically. For example, with a single fabric pack load, chamber pressure drops quickly so that, if evacuation is terminated at a fixed vacuum level, adequate exposure to vacuum may not be provided for proper removal of air which has been absorbed on or is clinging to the fabric. Therefore, fixed pressure excursions during pulsing alone may not provide the desired effectiveness or the efficiency of a reasonable number of pulses when working with all types of loads. With a full fabric load, chamber pressure drops more slowly so that the desired vacuum level may not be attained if evacuation is terminated on the basis of a fixed evacuation time.

The invention provides data to indicate characteristics of load being encountered to enable automated and accurate conditioning control, without requiring operator prejudgement of load or load contact sensors. The invention teaches the use of the slope of the depressurization curve during a cyclic pulse to evaluate the load. A specific method taught coordinates measurements of rate of depressurization which provide the functional input for a control logic decision on required parameters for proper conditioning of that load. In this way, vacuum exposure for proper air removal can be automatically and reliably provided for effective and efficient conditioning of both partial and full fabric loads.

Conditioning cyclic pulsing is provided through alternate evacuations and vapor pressurizations of the chamber. Since an objective is heating the load, the vapor should have high latent heat transfer upon condensation. Steam is the most commonly used condensable vapor having transferable latent heat but other vapors, e.g., vapors of organic solvents, such as alcohols, ketones, and ethers, can be used in conjunction with steam. During the evacuation portion of a cyclic pulse, the slope of the draw-down curve can be utilized to provide an accurate evaluation of load characteristics to enable load responsive automatic control. The slope of the draw-down curve can be obtained by measurement of changes in chamber pressure versus time. No load contact monitors are required and data is obtained solely through chamber pressure and time measurements; that is, through instrumentation which is reliable under the harsh conditions of a sterilizer environment.

Included in the concept of the present invention is analysis of the importance of air removal to proper load conditioning for steam heat sterilization. That is, air must be removed before steam can penetrate to condense and heat the load. But more unique in the invention is the realization of the inter-relationship of various fabric-related properties to load characteristics. For example, percentage of fabric in the load, chamber volume utilization, and packing procedures all have a fabric-related effect. This effect is manifested as a composite which most closely, short of use of actual load contact sensors, indicates load characteristics for purposes of proper control of the conditioning cycle. It has been discovered that this composite effect of fabric-related properties of a particular load is manifested most clearly while evacuating the chamber and is most accurately determined, and related to load conditioning, by measuring the rate of pressure change during selected portions of such evacuation.

In conditioning fabric-type loads, it has been discovered that there is a functional relationship between the slope of the evacuation phase pressure curve and the composite characteristics of the load. It has also been determined that there is a functional relationship between the slope of the evacuation phase curve and the percent of fabric in a full combination fabric-and-hardgoods load or the fractional part of a load occupied by fabric whether in a full or partial load. Further, it has been determined that these two functional relationships closely correspond to one another so that, for control purposes, the composite characteristics of any load or partial load may be related to or considered as the percent of a full load which is constituted of fabric.

The functional relationship between the slope of the evacuation phase pressure-time curve and the percent of fabric can be established empirically for any sterilizer employing a given evacuation system. This relationship can then be employed to relate the slope of any such curve to a percent of fabric which, in turn, can be employed to select the proper conditioning cycle and/or pressure-time parameters of the evacuation phase of the conditioning cycle for any load. For example, a curve representing this functional relationship may be established by plotting the percent of fabric against the slope of the evacuation phase pressure-time curve for loads having various known percentages of fabric. Load-contact sensors and instrumentation, utilizing known test procedures, can be employed to monitor the conditioning of test loads to establish a curve representing the functional relationship and to determine the pressure and time requirements for conditioning.

The empirically established functional relationship can be provided as a program input to control logic for a sterilizer. The control logic can include a mini-computer or microprocessor which uses this input to automatically control load conditioning. To accomplish this, monitored time and pressure inputs to the control logic can be employed to compute the slope of the evacuation phase pressure-time curve which is compared with the functional relationship program input to determine the cycle and/or pressure-time parameters required for conditioning. This information can also be employed in other phases of an overall sterilizing cycle, as, for example, during drying where the fabric content of a load has a direct bearing on required drying time.

Minimal fabric loads can require longer or higher vacuum treatment for air removal during conditioning because the pressure drop in the chamber is very rapid for such loads. Conversely, the relatively slow pressure drop in a chamber containing a full fabric load provides longer exposure to vacuum so that lower vacuum levels provide adequate air removal. For example, for a full fabric load in a standard 36-inch sterilizer, an evacuation time of up to five minutes or more may be required for the chamber to reach a pressure of 10" Hg vacuum, whereas, with a minimal fabric load in the same sterilizer, the 10" Hg vacuum pressure may be reached in less than one minute.

While conditioning may be controlled in accordance with the invention by controlling either time or pressure excursions, a combination of both may also be used. For example, time can be used as the controlling factor for minimal fabric loads, e.g., those loads which require less than one minute to reach a pressure of 10" Hg vacuum during evacuation, and pressure employed for controlling the evacuation phase of loads whose evacuation pressure-time curve slope indicates a higher percentage of fabric. This procedure avoids the necessity of using sophisticated and expensive vacuum measuring equipment capable of providing an analog output.

Pressure and time measurements can also be used directly in control without fixing the value of either. In a specific embodiment, minimum time and evacuation levels are established for each cyclic pulse. During the cyclic pulsing, only the upper pressure level, and consequently the upper temperature level, has a preselected or fixed value. The evacuation time and the lower pressure level can vary in a controlled manner.

Because of the data available in utilizing the teachings of the invention, the conditioning cycling can be optimized and the need for deep vacuum levels eliminated. Minimizing vacuum power requirements is an important contribution providing for use of effective, more economical and less complicated ejector apparatus in place of vacuum pumps. Reduction in both initial cost and operating power requirements result. This contribution of minimizing vacuum power requirements can be enhanced by flushing air from the chamber prior to cyclic pulsing. Such early addition of steam increases the efficiency of the ejector apparatus due to removal of air and the collapse of steam and also contributes to rapid and efficient heating of the load.

Other features, contributions, and advantages of the invention will be considered during the description of the accompanying drawings, in which.

In order to assure adequate conditioning during cyclic pressure pulsing, regardless of the nature of the load being conditioned, in accordance with one embodiment of the invention, both minimal evacuation time and minimal vacuum conditions must be met during the evacuation portion of a pulse before chamber evacuation is terminated and cyclic pressurization commenced. For example, sterilizers of the type and sizes generally employed in hospitals may be programmed to require an evacuation time of one minute and a vacuum level of at least 10" Hg. Under these conditions, chamber evacuation continues for a period of one minute, regardless of the rate of evacuation or the vacuum level attained. At the end of the preselected one-minute time, chamber pressure is checked and, if the vacuum is equal to or greater than 10" Hg, evacuation is terminated and pressurization immediately commenced.

However, if the evacuation rate has been such that the vacuum level is less than 10" Hg at the conclusion of one minute, the evacuation continues until this desired vacuum level is attained, regardless of the time requirement. Thus, for a heavy fabric load, the evacuation phase of a cyclic pulse may continue for four minutes or more before the desired subatmospheric pressure is attained; whereas, for a minimal fabric load the pressure within the chamber may be reduced to the minimal level prior to the expiration of one minute. By continuing evacuation for the required predetermined time for the minimal fabric loads, greater vacuum will be achieved, with the result that air within the load has an opportunity to escape and the pressure will be more nearly equalized throughout the load and chamber prior to steam pressurization.

Figure 1:
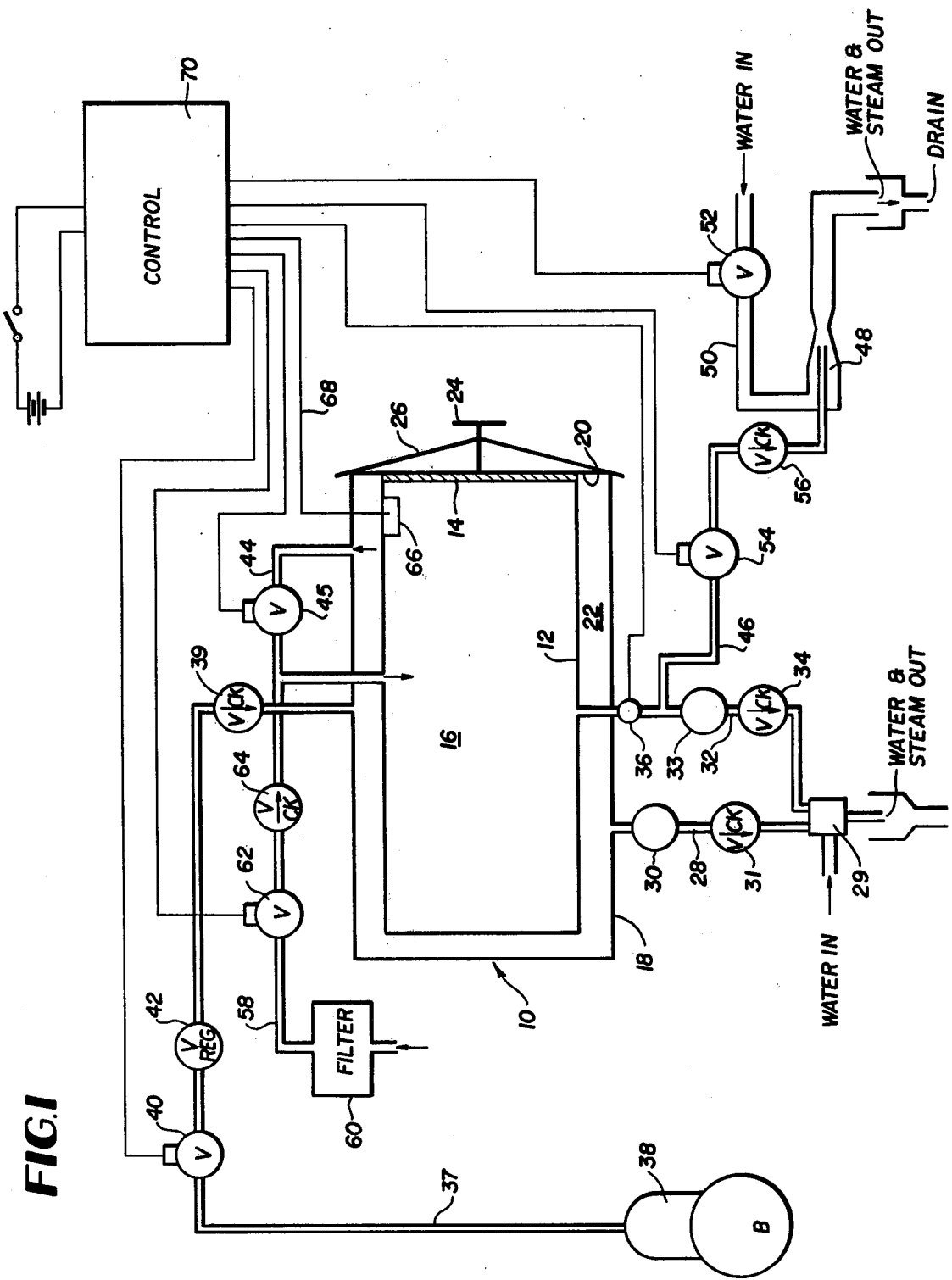
FIG. 1 is a schematic representation of sterilizing apparatus embodying the invention.

The invention can be practiced with conventional sterilizer chamber configurations and sizes. As shown in FIG. 1, a double-walled chamber structure, indicated generally at 10, includes an inner, open-ended vessel 12 defining with an end closure, door 14, a sterilizing chamber 15. Vessel 12 is supported with an outer wall 18 which is spaced outwardly from and circumscribes a major portion of vessel 12. An open end of the wall 18 is joined to the adjacent end of the inner vessel 12 by a flange 20 to define a steam jacket 22 between the inner and outer walls.

The door 14 can be hinged or otherwise mounted at one side of the open end of the double wall structure to facilitate opening and closing of the chamber 16. A conventional lock assembly can be used for door 14, e.g., a camlock assembly, including an actuating lever or wheel 24 and locking cams 26, enabling the door to be firmly locked to tightly seal the chamber 16 during the sterilizing operation.

The jacket 22 and chamber 12 are separately connected for discharge purposes, but interconnected in supply to provide certain advantages in load control. A drain pipe 28 connects the jacket 22 to a water-cooled heat exchanger 29 which discharges into a suitable drain. Heat exchanger 29 is supplied with cooling water which is mixed with the steam and hot condensate from the jacket to control the discharge temperature to a level acceptable for discharging into a conventional sewer drain. A steam trap 30 connected in drain pipe 28 removes condensate from the jacket 22 and a one-way check valve 31 prevents possible back-flow through line 28 into the jacket.

A second drain pipe 32 is connected between vessel 12 and heat exchanger 29. A steam trap 33 and one-way check valve 34 connected in drain pipe 32 control the flow of steam, condensate or other fluid from chamber 16 through the heat exchanger 29 to waste. A temperature sensing bulb 36 is mounted upstream of the steam trap 33 and adjacent the outer chamber wall 18 to measure the temperature of steam flowing from the sterilizing chamber 16 for control of steam supply during sterilizing.

A main steam supply line or conduit 37 connects a source of steam, such as boiler 38, to the steam jacket 22. One-way check valve 39, solenoid-actuated cut-off valve 40, and pressure regulator 42 are connected in the main steam line 37 to control the flow of steam into the jacket 22. Steam line 37 can have a plurality of branches, not shown, for admitting steam into the jacket at a plurality of locations. Pressure regulator 42 cooperates with steam trap 31 to maintain the pressure, and consequently the temperature, substantially constant in the jacket 22.

Steam is supplied to chamber 16 from the steam jacket 22. To accomplish this, a pipe 44 is connected to the outer wall 18 with its inlet in communication with the steam jacket, and to the wall 12 with its outlet in communication with the interior of sterilizing chamber 16. A solenoid-actuated valve 45 is connected in pipe 44 to control the flow of steam from the jacket to the sterilizing chamber. Supplying chamber steam from the jacket avoids many of the problems of low quality steam frequently encountered in operating sterilizers. Condensate and the like is collected in the jacket and utimately discharged from the bottom thereof through drain pipe 28, so that only substantially saturated steam enters chamber 16.

Chamber evacuation is accomplished through an evacuation conduit 46 connected to the drain line 32 upstream of steam trap 33. Conduit 46 has its outlet connected to a water ejector 48. Ejector 48 is supplied with water, at a uniform pressure through a pipe 50 and solenoid-actuated cut-off valve 52. Flow of water through the ejector 48 creates a suction in the end of conduit 46 to thereby evacuate the sterilizing chamber 16. Water supply line 50 discharges into a suitable drain, with the steam evacuated from chamber 16 being cooled by and condensed in the water before being discharged. Evacuator discharge can be supplied as the cooling fluid input to heat exchanger 29 in order to conserve water. Flow through the evacuation conduit 46 is controlled by a solenoid-actuated valve 54 and one-way check valve 56.

An air supply line 58 is connected to steam pipe 44 at a point downstream from valve 45. Air at atmospheric pressure is supplied through air line 58 and a filter 60 to chamber 16 upon completion of a sterilizing cycle. Filter 60 is of a type to effectively remove bacteria as well as dust and the like from the air, and can also include air sterilizers. Flow through the filter and air line is controlled by a solenoid-actuated shut-off valve 62 and one-way check valve 64.

Pressure sensor assembly 66, capable of sensing pressures both above and below atmospheric, is mounted within chamber 16. Pressure sensor assembly 66 is connected, through suitable conductors indicated generally at 68, to a master logic control 70 which controls operation of the apparatus.

Figure 2:
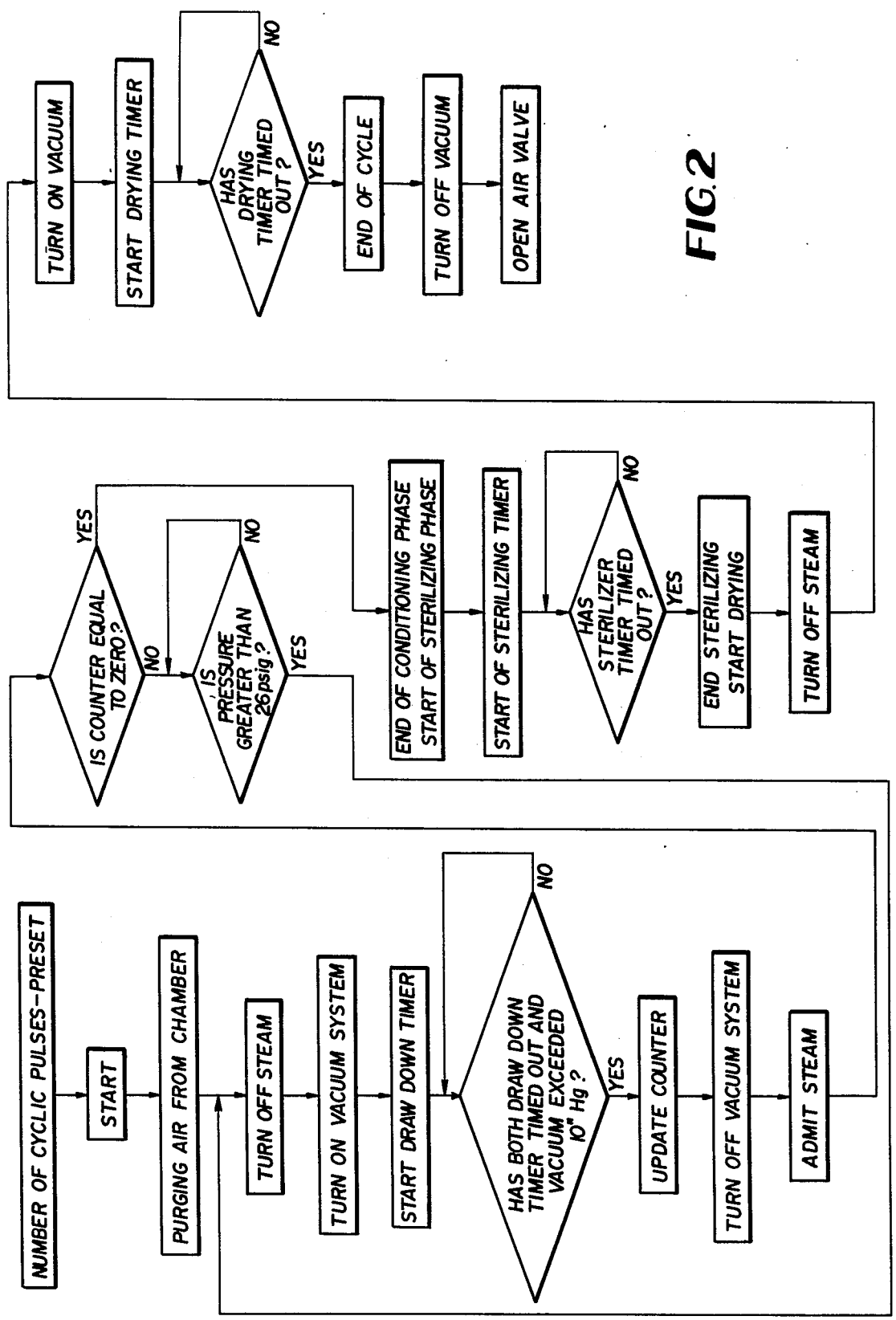
FIG. 2 is a process flow chart for carrying out a sterilizing cycle in accordance with the invention, utilizing the apparatus of FIG. 1.

Operation of the sterilization apparatus with cyclic pulses controlled to have a minimum evacuating time and reach a selected vacuum level is outlined in the flow chart of FIG. 2. The cycle can include initially purging air from the chamber and then subjecting the material to a fixed number of cyclic pulses of pressure below a predetermined upper level by alternately evacuating the chamber and pressurizing it with conditioning vapor. At the conclusion of the conditioning pulsing, the chamber is pressurized with steam to a level producing the desired sterilization temperature, and maintained at this temperature (which can be accomplished by a pressure measurement if no air is present) for a predetermined time. Next, the sterilization chamber is evacuated and maintained at a relatively high vacuum for a predetermined time, for example five minutes, to dry the material. Finally, the chamber is brought to atmospheric pressure by the admission of air by passing atmospheric air through a bacterial filtering system.

It is preferred to initiate conditioning by introducing steam at supra-atmospheric pressure to the sterilization chamber while simultaneously operating the evacuating system. When air is purged from the chamber in this way, pressure in the chamber initially increases until the increased proportion of steam in the steam-air mixture being evacuated increases the efficiency of the selected ejector system to the point that chamber pressure starts to decrease.

As part of the process depicted in FIG. 2, this decrease in pressurization rate can be sensed and employed to generate a signal, with or without a time delay, closing steam valve 45. Or a purge timer can be started at the initiation of steam injection or evacuation. Evacuation is continued, after the purge step, until the pressure sensor 66 senses that a predetermined subatmospheric pressure, for example 10" Hg, has been reached and the time requirement has been satisfied. When these conditions have both been met, a conditioning pressure pulse counter is up-dated, the evacuating system is turned off, and steam valve 45 is opened to admit steam into the chamber from jacket 22 to bring the pressure within the chamber up to the predetermined upper pressure level.

If the conditioning pulse counter signals that the load has been subjected to the proper number of pressure pulses, the conditioning phase of the cycle is ended. If the counter indicates that this number has not been reached, steam valve 45 is closed, the evacuating system turned on, and the evacuating draw-down timer is again started to subject the system to another pressure pulse as just described. In the specific embodiment set forth, the load is subjected to a predetermined plurality of pressure pulses. Pulse counting can take place at lower or upper pressure levels.

In the later sterilization phase of the cycle, steam pressure within the chamber is maintained at the desired level, for example 26-30 psig, to maintain a required sterilization temperature for a predetermined time. At the end of the sterilization time, the evacuation system is turned on and operated for a predetermined time, preferably maintaining the vacuum during this time at the maximum level attainable by the evacuating system, to effectively dry the material in the chamber. Then solenoid-actuated valve 62 in air line 58 is opened, permitting filtered air to enter the chamber. When the pressure within the chamber is substantially equal to ambient atmospheric pressure, the cycle is complete and the door 14 can be opened.

The pressure sensor assembly 66 may be a conventional transducer capable of continuously sensing chamber pressure and transmitting an electrical signal proportional to the instantaneous pressure. This signal can then be used by the system control logic to determine rate of pressure change, or the pressure-time curve slope, to control actuation of the various process phases. Alternatively, the pressure sensor assembly 66 can contain a plurality of sets of contacts, one which is actuated when the pressure within the chamber reaches a predetermined subatmospheric pressure, for example, 10" Hg vacuum, and a second which is actuated at the sterilization pressure, for example, 26 psig. These signals, in combination with the time signals from suitable conventional timers within the control logic 70, can be utilized to automate control of time and pressure parameters during the conditioning phase. Load responsiveness is thus provided by the vacuum levels and the time required to reach such levels which will depend on the nature of the load.

Figure 3:
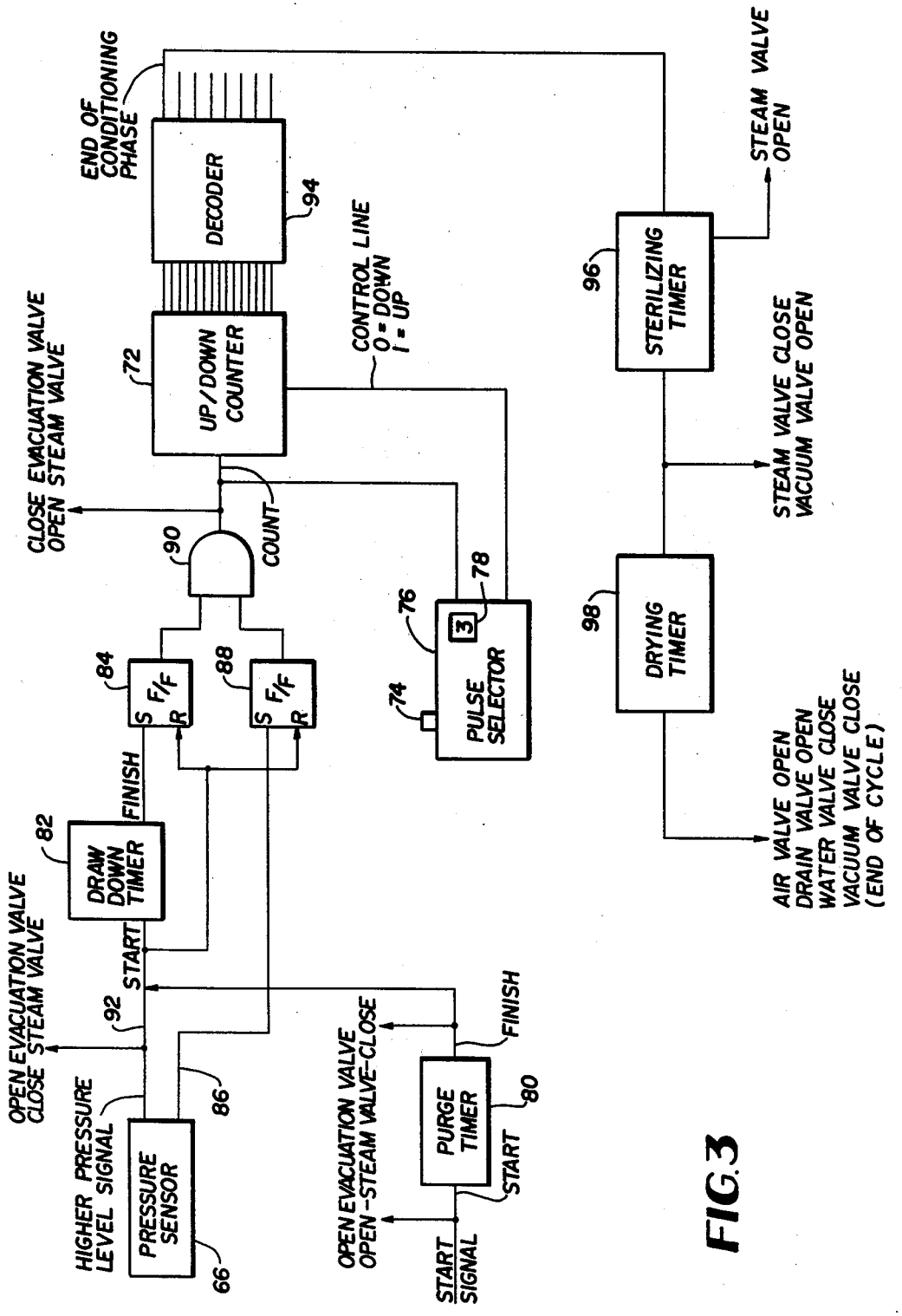
FIG. 3 is a schematic representation of a control logic for controlling apparatus in accordance with the invention.

The electronic control of the system illustrated in FIG. 3, includes a conventional up-down counter 72 which may be up-counted by a signal on the "count" line when the "control" line is in a given state and down-counted by a signal on the "count" line when the "control" line is in a different given state. Before the process is begun, up-down counter 72 is pre-loaded with a number which corresponds to the number of chamber evacuations to be employed.

Counter 72 can be loaded by depressing button 74 on the pulse selector 76. Pulse selector 76 can be a conventional pulse generator arranged so that the number of times that button 74 is depressed appears at display window 78. Each time button 74 is depressed, pulse selector 76 is effective to generate a pulse on both the count line and the control line input to counter 72 and the counter is arranged so that it will up-count when a signal is present on the control line. In the embodiment shown, button 74 has been pressed to load the number three into counter 72. Up-down counter 72 can be automatically pre-loaded with the fixed number required, thereby removing from the operator's control any possible margin of error in improperly loading the up-down counter.

A start signal is generated by a known means, such as closing a conventional on-off switch connected in the main power circuit. When air is to be flushed from the chamber, the start signal causes the purge phase to begin. While the length of the purge and the maximum pressure attained during the purge phase may be controlled in a number of ways, as described above, FIGS. 3-5 illustrate the simplest mode of control, that is, a predetermined period of time.

The start signal is thus effective to start purge timer 80, which can be a conventional timer such as a digital timer, and which is arranged to emit a signal on the "finish" output line a predetermined period of time after a signal is fed to the "start" input line. The start signal input is also electrically connected to the electric control solenoid means of valves 52 and 54 (FIG. 1) of the evacuation system and to steam supply valve 45 to open these valves. Steam is admitted and the chamber is evacuated simultaneously. After a predetermined period of time, purge timer 80 times out and emits a signal on the "finish" output line which is effective to close steam valve 45.

Referring to FIG. 3, the "finish" output line of purge timer 80 is also connected to the "start" input of draw-down timer 82. The evacuation phase of the cyclic conditioning pulses continues until at least a predetermined vacuum level has been reached and a predetermined period of time has lapsed. In this embodiment, draw-down timer 82 can be started at the beginning of the steep negative-slope portion of the pressure curves of FIGS. 4 and 5 which corresponds to the time of closing of steam valve 45. Other points can be used;

starting the draw-down timer at about four psig is representative.

Draw-down timer 82, for the minimum parameters embodiment being described, is similar to purge timer 80, and emits a signal on its output (or finish line) a predetermined period of time after a signal is fed to its input line. The output signal of draw-down timer 82 is fed to the set input of flip flop 84.

As stated above, pressure sensing assembly 66 can include a first set of contacts arranged to emit signals when the upper preselected pressure is reached or exceeded and a second set which emits signals when the lower preselected pressure level is reached or exceeded. As shown in FIG. 3, the signals are emitted on respective output lines, and assembly 66 can comprise two separate pressure responsive switches or other sensing devices connected to respective signal generating circuits. When the lower preselected pressure is attained, a signal is emitted on line 86 which is fed to the set input of flip flop 88.

Set-reset flip flops 84 and 88 are effective to emit an output signal on their respective output lines when a signal is received on the set input lines, and to hold the signal on the output line until the flip flops are reset. The outputs of the flip flops are connected to the inputs of AND gate 90, and when both of the flip flops are set at the same time, AND gate 90 is effective to feed a signal to the "count" input of up-down counter 72. This will occur only when the pressure has reached or exceeded the predetermined lower level and the draw-down timer 82 has timed out indicating that the negative-slope portion of the cycle has lasted for the predetermined minimum time. If only one of these two conditions are present, then there will be an output on only one of the flip flops, and consequently there will be no output signal at the output of AND gate 90.

The output of AND gate 90 is also connected to steam valve 45 and to evacuation valve 54, and is effective to respectively open the steam valve and close the evacuation valve, so that steam enters and pressurizes the chamber upon satisfaction of both the evacuation time and pressure parameters.

Assuming that the up-down counter 72 is not at zero, when the preselected higher pressure is exceeded, sensor 66 is effective to generate an output signal on line 92 which also is connected to evacuation valve 54 and steam valve 45. This signal is effective to respectively open the evacuation valve and close the steam valve to cause the chamber pressure to drop. The occurrence of a signal on line 92 is further effective to set draw-down timer 82 which, as described above, emits an output signal on the "finish" line thereof when the predetermined time period has elapsed, and to reset flip flops 84 and 88.

The cyclic pulses continue in the above-described manner until the preselected number of cyclic pulses have occurred. The outputs of up-down counter 72 are connected to decoder 94, each output line of which is representative of a given number. Thus, at the time that the initial number of pulses are loaded into counter 72, the corresponding output line of decoder 94 has a signal thereon. When this initial number of pulses is counted down to zero, then the zero output line of decoder 92 has a signal thereon. This indicates the end of the conditioning phase, and the signal on the output of the zero line of the decoder, which is connected to a sterilizing timer 96, initiates the sterilizing phase.

Sterilizing timer 96 maintains an output signal on a line connected to the control solenoid of steam shut-off valve 45 in conduit 44 between jacket 22 and chamber 16. The timer includes temperature level control means connected in the line to valve 45 to control the flow of steam into the chamber. The temperature level control means includes temperature sensor 36, which transmits a signal proportional to the temperature of steam flowing from the chamber. The signal from temperature sensor 36 is employed to control the opening and closing of the normally closed valve 45 to maintain the temperature within the chamber at the desired level within predetermined limits.

The pressure within chamber 16 can also be employed to control opening and closing of valve 45 during the sterilizing phase of the cycle. However, generally, temperature sensing means are preferred for economic reasons for controlling sterilizing steam flow.

When sterilizing timer 96 times out, a signal is emitted on its finish line to start a drying phase timer 98. Simultaneously, steam valve 45 is closed and vacuum valve 54 is opened. Drying timer 98 maintains the system in this condition for a predetermined time effective to dry the load. When drying timer 98 times out, it emits a signal on its finish line to close evacuation system valves 52, 54. At the same time, air valve 62 is opened, admitting filtered air into the chamber 16 to complete the cycle.

Figure 4:
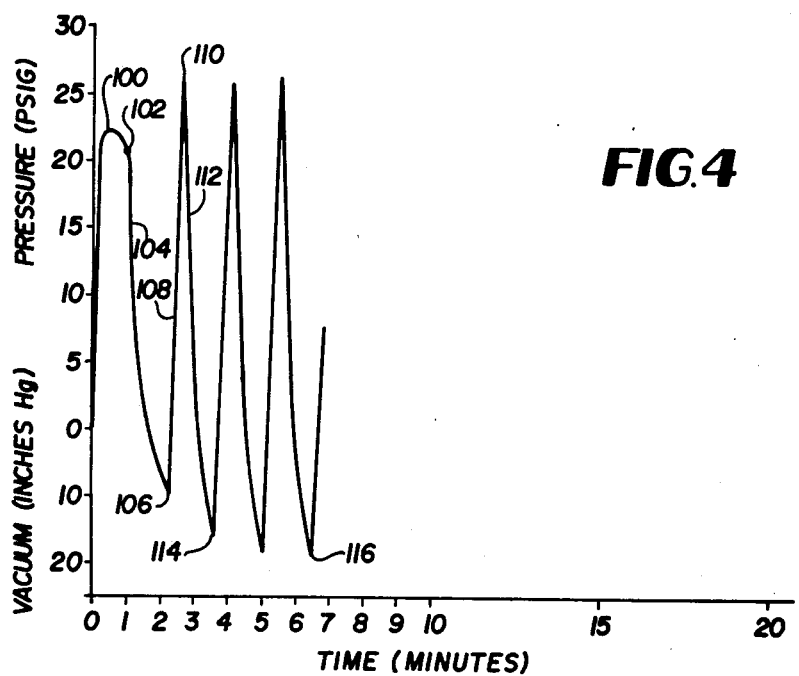
FIG. 4 is a graphic representation of pulse configuration achieved during load conditioning of a minimal fabric type load in accordance with the invention.
Figure 5:
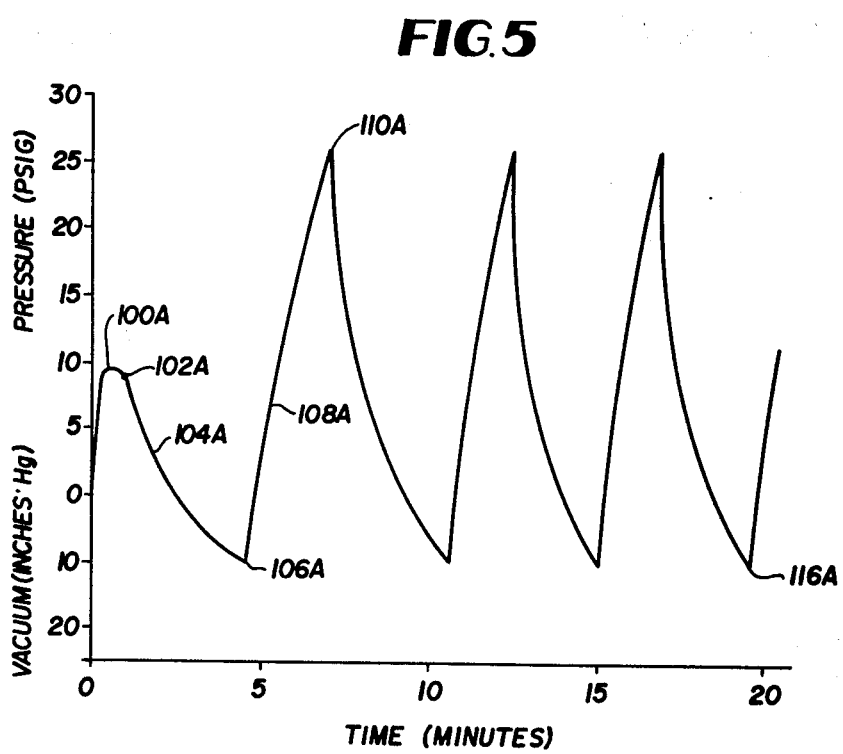
FIG. 5 is a graphic representation of the pulse configuration achieved during load conditioning of a full fabric type load in accordance with the invention.

FIGS. 4 and 5 are graphic representations of chamber pressure, plotted against time, during operation of the apparatus described above in accordance with the process of the invention wherein the purge phase of the sterilizing cycle is terminated after a predetermined time. FIG. 4 represents the purging and conditioning phases of the cycle employed to sterilize a minimal fabric load, and FIG. 5 represents operation of the same sterilizer with a full fabric load.

At the start of the cycles represented in both FIGS. 4 and 5, the introduction of steam under pressure into the chamber 16 while simultaneously operating the evacuating means results in a relatively sharp initial increase in pressure. With the minimal fabric load depicted in FIG. 4, the pressure builds rapidly to above 20 psig before the ejector apparatus is able to halt the pressure increase at point 100 on the pressure curve. At this point the pressure starts to fall gradually under the influence of the ejector while steam continues to be admitted. Purge timer 80, which has been set for a one-minute purge time, times out at point 102, and closes the steam valve 45. At the same time, draw-down timer 82 can be started.

The pressure drops from point 102 along curve section 104 to the minimum vacuum level (which has been pre-set at 10" Hg) at point 106. Approximately 1.3 minutes are required, after the purge phase, to reach the minimum vacuum level from point 102 in the embodiment shown. Thus, when drawdown timer 82 timed out at the end of one minute and emitted a signal to flip flop 84, flip flop 88 has not yet received a signal from the lower pressure contacts in pressure sensor 66. When this low pressure was sensed, resulting in a signal along line 86 to flip flop 88, AND gate 90 passed a signal to the up-down counter 72 to count it down one count, and simultaneously signalled the closing of the evacuation valve 54 and the opening of steam valve 45. This condition remained stable along curve segment 108 from the minimum vacuum point 106 to the maximum chamber pressure of approximately 27 psig at point 110. Note that the pressure rise between points 106 and 110 is very rapid, following an almost straight line and requiring slightly less than one-half minute. The slope of the pressurization curve can be thought of as indicative of the heat absorption characteristics of the load while the evacuation phase slope is generally considered more indicative of air removal properties.

Upon sensing the maximum pressure, sensor 66 emits a high pressure level signal along line 92 to simultaneously open evacuating valve 54, close steam valve 45, start drawdown timer 82, and re-set flip flops 84 and 88. In this condition, evacuation continued from point 110 along curve segment 112 to low pressure point 114. Note, however, that point 114 is at approximately 16" Hg vacuum, or approximately 6" Hg below point 106. This occurred because, when sensor 66 sensed the pre-set low pressure of 10" Hg and emitted a signal on line 86 to flip flop 88, the draw-down timer 82 had not yet timed out and emitted a signal to flip flop 84. Continued evacuation for a full minute resulted in the load within the chamber being subjected to an increased vacuum, thereby further assuring adequate withdrawal of air from the interstices of the fabric load.

This procedure was repeated for three full pressurization and evacuation pulses of the conditioning phase, at the conclusion of which the up-down counter was down-counted for the fourth time as the pressure within the chamber reached the point 116 on the curve. At this point, decoder 94 emitted a signal starting sterilizing timer 96 and opening the steam valve 45 to increase the pressure and the temperature within the sterilizer to the desired sterilizing temperature. The chamber pressure curve for the remaining porton of the cycle is not shown in FIG. 4 or 5, since its configuration should be evident from earlier description.

Comparing curve section 104a of FIG. 5 with the corresponding section 104 of FIG. 4 demonstrates the automatic selection of conditioning tailored to the particular load. Thus, for the full fabric load of FIG. 5, after one minute of evacuation time, from point 102a, the pressure within chamber 16 has only dropped to approximately atmospheric pressure. An additional 2.6 minutes, or a total of 3.6 minutes, evacuation time was required to reach a vacuum of 10" Hg from 9½ psig, as compared with 1.3 minutes required to reach 10" Hg vacuum from approximately 21 psig for the minimal fabric load. The relatively slower rise in chamber pressure during the flushing phase for the full fabric load, as compared to the minimal fabric load, is due to the differing absorptive characteristics of the loads.

Similarly, the substantially greater evacuation times required in FIG. 5 result from the increased time required, especially during early pulses, to draw air from the interstices of the full fabric load. Subjecting the full fabric load to evacuation for an increased period of time results in a more efficient removal of air. However, such additional evacuation time is not required, and therefore not used, for the minimal fabric loads. The resulting savings in time and operating expenses should be apparent. It should also be apparent that a gradient of evacuating phase times is available between minimal fabric and full fabric loads and that the proper time for the particular load is automatically selected by this embodiment.

The load responsive aspects of the invention make possible the use of relatively low level vacuums while assuring proper air removal and heating throughout the load. As shown in FIG. 5, a partial vacuum of only 10" Hg is satisfactory for carrying out the invention, and the evacuation phase of each pressure pulse is terminated at this level. However, as shown in FIG. 4, when utilizing this embodiment to condition a minimal fabric load, this minimum vacuum level may be reached before adequate air removal from any fabric present is achieved and, in accordance with the invention, the load is subjected to a continuing vacuum, preferably at an increasing level, for a predetermined minimum time.

The load dependent aspects of the invention are also evident from the pressurization phases which follow initial air flushing. Thus, from the initial low level point 106a of FIG. 5 to the initial maximum or high pressure level 110a, the section of curve 108a requires slightly more than 2½ minutes, as compared with less than one-half minute for the corresponding pressurization phase of the minimum fabric load in FIG. 4. Note, also, that the total time required to complete the conditioning phase, including the one-minute steam pressurization during flushing, and three complete pressurization-evacuation pulses is slightly less than seven (7) minutes for the minimum fabric load, as compared with almost twenty (20) minutes required for the full fabric load.

There are advantages, in addition to facilitating use of ejector apparatus instead of a vacuum pump, in the selection of a relatively low vacuum level objective (such as 10" Hg). Such low level vacuum increases the overall efficiency of a sterilizer and conserves energy by minimizing heat losses. High vacuum evacuation when the load is being heated by steam removes heat from the load and the sterilizer walls. Therefore, it is advantageous in decreasing heat losses to be able to condition the load with as little vacuum as possible consistent with rapid heat-up and proper air removal.

Pressure transducers can be used to monitor chamber pressure to provide information indicative of load characteristics and which can be used, in accordance with the invention, for the automatic selection of conditioning pressure and/or time, or even to select the cycle for conditioning that load. The functional relationship between the slope of the evacuation phase pressure-time curve for various loads processed in a particular sterilizer employing a given evacuation system can be programmed into the control logic and employed to select the desired conditioning pressure-time parameters based on a comparison of collected data with the functional relation derived empirically from pre-established or projected data from loads over a range of characteristics. The empirically established functional relationship is programmed into the control logic and employed as a basis for comparison of the slope of the evacuation phase curve computed from the monitored pressure input from the transducer and time input from conventional time signal generator means in the control logic.

Slope comparison for conditioning control preferably is carried out near atmospheric pressure in the evacuation phase, but average slope over a longer portion on all of the evacuation phase can also be employed. For example, it has been determined that, for a standard 36-inch sterilizer, when the slope of the evacuation pressure curve indicates an evacuation rate greater than about 9 psi/min., when determined between about 4 and 0 psig during an evacuation phase, the chamber pressure will reach a vacuum level of 10" Hg in less than one minute, and a control logic decision can then be made to continue the evacuation phase for a full minute. Conversely, a slope which indicates an evacuation rate less than 9 psi/min., indicates that more than one minute will be required to reach a vacuum level of 10" Hg, and the control logic decision is to terminate the evacuation phase of the pulse only when this minimum vacuum level is reached.

Test loads for the evaluation of the invention included sheet challenge packs, towel challenge packs, government surgical packs, and hardgoods packs.

Several criteria were evaluated in the qualification testing of conditioning and sterilizing in accordance with the invention. Sterilization efficacy was demonstrated in full loads and single packs of fabrics, wrapped hardgoods, and unwrapped hardgoods. As an example of one test procedure, in each of five (5) consecutive cycles, biological indicators had to be rendered sterile, with an adequate safety margin demonstrated. The condition of the sterilized loads had to be dry, undamaged, and substantially free of visible wet-spotting on outer wrappers, or stains or residue on metal surfaces when recommended loading practices are followed. A further criterion was that all applicable government test specifications be achieved. For example, for a 24"×36"×60" sterilizer, Federal specification GG-S-1343A specifies particular sized loads of surgical packs, and hardgoods, and also specifies allowable total cycle time for all such loads. Other criteria relating to sterility, drying criteria, pressure, and temperature tolerances were met.

These criteria were met while assuring that performance characteristics, production cost, and operating economies were all favorably comparable with present commercial sterilizers, when connected to utilities which would be encountered in normal operations.

During testing, temperatures were measured by a plurality of Type T (copper constantin) Teflon-insulated thermocouples, and pressure was monitored by Viatran absolute pressure measuring transducers. Temperature and pressure were continuously monitored and recorded.

Carefully tested biological and chemical indicators were packed in the test packs. The biological indicators were SPORDI biological spore strips produced by American Sterilizer Company of Erie, Pa. Chemical indicators used were American Sterilizer Company CHEMDI test indicators. These chemical indicators change color to indicate complete load conditioning and steam penetration.

For evaluation test purposes, thermocouples were packed in the central portion of the packs, in the vicinity of the chemical indicators and biological test strips, so that pack temperatures were monitored along with chamber temperatures. In the case of hardgoods, the thermocouples were placed in direct metal-to-metal contact with the heaviest instruments or components of the pack, and chemical and biological indicators were distributed throughout the pack contents. Times were double-checked with stop-watches, with the times being compared to assure repeatability.

In the test of five consecutive single pack and full loads of wrapped hardgoods, towel packs, sheet challenge packs, and ten-sheet government packs, sterility was produced in all test indicators processed. None of the packs processed exhibited any evidence of water spotting on the external wrappings following a cycle with a five-minute drying period. All fabric challenge packs were well within the allowable standards for drying efficiency.

Temperatures within the center of the packs, for both full and minimal loads, were substantially equal to chamber temperatures before completion of the conditioning phase of the cycle.

Test cycles were run wherein the sterilization phase extended for a full recommended four minutes and for abbreviated periods. Biological test strips processed indicated sterility for both the full and abbreviated cycles, indicating an adequate margin of safety. Chemical indicators showed steam penetration throughout the loads in each case.

While specific embodiments of the invention have been disclosed and described, it is to be understood that the invention is not intended to be restricted to such embodiments but, rather, all embodiments which, in view of the present teaching, come within the spirit and scope of the invention.

We claim:

1. Apparatus for conditioning materials forming a load within a sealable sterilizing chamber capable of operation at pressure above atmospheric for steam sterilization without requiring selection of quantity or characteristics of the materials, such conditioning including removal of air, moistening the load, and heating of the load to a desired temperature in preparation for sterilization, the apparatus comprising:

evacuation means operable to evacuate the sterilizing chamber, vapor injection means operable to inject a vapor having a transferrable latent heat into the sterilizing chamber, and control means controlling operation of the evacuation means and the vapor injection means to provide cyclic pulsing of chamber pressure to provide a plurality of cyclic pulses of chamber pressure below an upper pressure level related to desired temperature for sterilization, each cyclic pulse including an evacuating phase during which pressure in the chamber is decreasing during operation of the evacuation means and a vapor injecting phase during which pressure within the chamber is increasing during operation of the vapor injecting means, pressure sensing means monitoring chamber pressure change during cyclic pulsing, timing means for measuring the time of the evacuation phase of the cyclic pulses, and such control means including means responsive to such indication of chamber pressure and evacuation time for determining the rate of evacuation of the chamber and for automatically controlling such cyclic pulsing in response to the determined chamber evacuation rate to complete the conditioning of the load.

2. Apparatus for conditioning materials forming a load within a sealable sterilizing chamber capable of operation at pressure above atmospheric for steam sterilization without requiring selection of quantity or characteristics of the materials, such conditioning including removal of air and heating of the load to a desired temperature for sterilization, the apparatus comprising:

evacuation means operable to evacuate the sterilizing chamber, steam injection means operable to inject steam into the sterilizing chamber, means operating the evacuation means and the steam injection means to provide cyclic pulsing of chamber pressure including a plurality of cyclic pulses of chamber pressure below an upper pressure level related to desired temperature for sterilization, each cyclic pulse including an evacuating phase during which pressure in the chamber is decreasing during operation of the evacuation means and a steam injecting phase during which pressure within the chamber is increasing during operation of the steam injecting means, pressure sensing means monitoring chamber pressure change during a cyclic pulse, timing means for measuring the time of each evacuation phase, and pulse cycle control means for controlling such cyclic pulsing responsive to such indication of chamber pressure and evacuation time, such control of cyclic pulsing including control of the means operating the evacuation means to continue each evacuation phase of the cyclic pulse until both a predetermined time has lapsed and a predetermined vacuum level is reached in the sterilizing chamber and control of the steam injecting means during cyclic pulsing to heat the load to the desired sterilization temperature and to remove air from throughout the sterilizing chamber irrespective of load size and load characteristics.

3. The apparatus of claim 2 including means for initiating load conditioning by injecting steam into the chamber while simultaneously evacuating the chamber to flush air from the chamber.

4. An apparatus for conditioning and sterilizing goods within a sterilizing chamber capable of operating at internal pressures above atmospheric for steam sterilization following conditioning of a load of goods in the chamber, the conditioning including the removal of air from the chamber and heating the load to a desired temperature, the apparatus comprising, steam injector means having a first electrically operated valve means operable between an open and a closed position to respectively pressurize the chamber and stop the flow of steam into the chamber, evacuating means including suction means and second electrically operated valve means operable between an open and a closed position to respectively connect the chamber to the suction means to evacuate the chamber and disconnect the chamber to stop the evacuation, the first and second electrically operated valve means being operable to alternately evacuate and inject steam into the chamber to subject a load of goods in the chamber to a plurality of cyclic pressure pulses below an upper pressure level corresponding to the desired sterilization temperature, control means controlling operation of the steam injection means and the evacuation means, the control means including, timing means for timing the evacuation of the chamber following each operation of the first electrically operated valve to the open position, pressure sensing means sensing the pressure within the chamber, means responsive to both the timing means and the pressure sensing means for maintaining the second electrically operated valve in the open position upon each opening thereof until both a predetermined time has lapsed and a predetermined lower pressure has been attained in the chamber, means for closing the second electrically operated valve means and opening the first electrically operated valve means to inject steam into and pressurize the chamber after the passing of the predetermined time and the attainment of the predetermined lower pressure, means responsive to the pressure sensing means for closing the first electrically operated valve means and opening the second electrically operated valve means to again evacuate the chamber, the control means being operable to repeat the evacuating and pressurization phases of the cyclic pressure pulses, and counting means operable to terminate the cyclic pressure pulsing after a predetermined number of such pulses.

5. The invention as defined in claim 4 wherein the control means further comprises means for initially opening both the first and second electrically operated valve means to simultaneously admit steam into the chamber and evacuate the chamber to thereby purge air from the chamber.

6. The invention as defined in claim 5 further comprising means for closing only the first electrically operated valve means after a predetermined time following the initial opening of both the first and second electrically operated valve means to thereby commence the evacuation phase of the first cyclic pressure pulse.

* * * * *